(12) United States Patent
Phillips

(10) Patent No.: US 6,406,500 B1
(45) Date of Patent: *Jun. 18, 2002

(54) FOOT PROSTHESIS HAVING CURVED FOREFOOT

(76) Inventor: Van L. Phillips, 4702 San Jacinto Ter., Fallbrook, CA (US) 92028

( * ) Notice: Subject to any disclaimer, the term of this patent is extended or adjusted under 35 U.S.C. 154(b) by 0 days.

This patent is subject to a terminal disclaimer.

(21) Appl. No.: 09/432,036

(22) Filed: Nov. 2, 1999

Related U.S. Application Data (63) Continuation of application No. 08/727,772, filed on Oct. 8, 1996, now Pat. No. 5,976,191, which is a continuation of application No. 08/532,530, filed on Sep. 22, 1995, now Pat. No. 5,593,457, which is a continuation of application No. 08/270,231, filed on Jul. 1, 1994, now Pat. No. 5,486,209, which is a continuation of application No. 07/977,654, filed on Nov. 17, 1992, now abandoned, which is a continuation of application No. 07/337,374, filed on Apr. 13, 1989, now Pat. No. 5,181,932.

(51) Int. Cl.[7] .................................................. A61F 2/66
(52) U.S. Cl. ....................................................... 623/55
(58) Field of Search ...................................... 623/47–56

(56) References Cited

U.S. PATENT DOCUMENTS

| 61,780 A | 1/1867 | Watson |
|---|---|---|
| 65,187 A | 5/1867 | Emery |
| 277,562 A | 5/1883 | Furrer |
| 366,494 A | 7/1887 | Marks |
| 693,400 A | 2/1902 | Jochimsen |

(List continued on next page.)

FOREIGN PATENT DOCUMENTS

| DE | 295807 | 12/1916 |
|---|---|---|
| DE | 308671 | 10/1918 |
| DE | 325171 | 9/1920 |
| DE | 379849 | 8/1923 |
| DE | 807214 | 6/1951 |

(List continued on next page.)

OTHER PUBLICATIONS

"The Seattle Prosthesis Foot—A Design for Active Sports: Preliminary Studies," E.M. Burgess, M.D., et al., Orthotics and Prosthetics Journal, vol. 37, No. 1, Spring 1983.
The Seattle Foot—Winner of Presidential Design Aware—Jan. 30, 1985.

(List continued on next page.)

*Primary Examiner*—David H. Willse
(74) *Attorney, Agent, or Firm*—Knobbe, Martens, Olson & Bear LLP

(57) ABSTRACT

A foot prosthesis is provided for attaching to a pylon or other intermediate supporting member fitted to the stump of an amputee. The foot prosthesis includes a forefoot portion constructed of a resilient polymer-encapsulated fiber laminate and having an upper attachment section, a curved intermediate section and a lower forward extending section. The shape of the forefoot is generally parabolic or J-shaped so as to provide smooth resilient support to the amputee during normal walking and running activities without producing undue stress concentration in the prosthetic foot, which could otherwise degrade the integrity of the foot. An arcuate toe section provides smooth rolling contact of the foot prosthesis with a ground surface during toe-off, simulating the stride and feel of a natural human foot. A heel portion, also formed of a resilient polymer encapsulated laminate material, attaches under the forefoot in order to provide enhanced comfort and energy absorption during heel-strike. The strength and resilience characteristics of the forefoot and heel portions may be adjusted by interchanging like elements so as to accommodate amputees having different sizes, weights and activity levels.

8 Claims, 4 Drawing Sheets

U.S. PATENT DOCUMENTS

| | | |
|---|---|---|
| 708,685 A | 9/1902 | White |
| 809,875 A | 1/1906 | Wilkins |
| 817,340 A | 1/1906 | Rosenkranz |
| 809,876 A | 4/1906 | Wilkins |
| 827,720 A | 8/1906 | Erwin |
| 951,989 A | 3/1910 | Hanger |
| 1,013,828 A | 1/1912 | Thomas |
| 1,071,230 A | 8/1913 | Hanger |
| 1,128,018 A | 2/1915 | McFarland |
| 1,151,144 A | 8/1915 | Wofe et al. |
| 1,294,632 A | 2/1919 | Dickson |
| 1,352,943 A | 9/1920 | Dodge |
| 1,424,264 A | 8/1922 | Shrodes |
| 1,804,915 A | 5/1931 | Collins |
| 2,036,830 A | 4/1936 | Rowley |
| 2,075,583 A | 3/1937 | Lange |
| 2,126,654 A | 8/1938 | Morris |
| 2,197,093 A | 4/1940 | Campbell |
| 2,379,538 A | 7/1945 | Meierhofer |
| 2,440,075 A * | 4/1948 | Campbell ............... 623/50 |
| 2,453,969 A | 11/1948 | Carter |
| 2,475,372 A | 7/1949 | Catranis |
| 2,543,908 A | 3/1951 | Guzey |
| 2,556,525 A | 6/1951 | Drennon |
| 2,570,735 A | 10/1951 | Weise |
| 2,619,652 A | 12/1952 | Vesper |
| 2,692,392 A | 10/1954 | Bennington |
| 2,699,554 A | 1/1955 | Comelli |
| 2,899,685 A | 8/1959 | Bourcier de Carbon |
| 3,335,428 A | 8/1967 | Gajdos |
| 3,400,408 A | 9/1968 | Garcia |
| 3,438,587 A | 4/1969 | Jackson, Jr. |
| 3,538,516 A | 11/1970 | Bailey et al. |
| 3,707,731 A | 1/1973 | Morgan |
| 3,754,286 A | 8/1973 | Ryan |
| 3,833,941 A | 9/1974 | Wagner |
| 3,874,004 A | 4/1975 | May |
| 3,889,301 A | 6/1975 | Bonner, Sr. |
| 3,890,650 A | 6/1975 | Prahl |
| 3,953,900 A | 5/1976 | Thompson |
| 4,007,496 A | 2/1977 | Glabiszewski |
| 4,089,072 A | 5/1978 | Glabiszewski |
| 4,091,472 A | 5/1978 | Daher et al. |
| 4,128,903 A | 12/1978 | Marsh et al. |
| 4,161,042 A | 7/1979 | Cottingham et al. |
| 4,177,525 A | 12/1979 | Arbogast et al. |
| 4,180,872 A | 1/1980 | Chaikin |
| 4,225,982 A | 10/1980 | Cochrane et al. |
| 4,268,922 A | 5/1981 | Marsh et al. |
| 4,302,856 A | 12/1981 | May |
| 4,306,320 A | 12/1981 | Delp |
| 4,314,398 A | 2/1982 | Pettersson |
| 4,328,594 A | 5/1982 | Campbell et al. |
| 4,360,931 A | 11/1982 | Hampton |
| 4,370,761 A | 2/1983 | Serri |
| 4,395,783 A | 8/1983 | Eyre et al. |
| 4,397,048 A | 8/1983 | Brown et al. |
| 4,459,709 A | 7/1984 | Lea et al. |
| 4,506,395 A | 3/1985 | Haupt |
| 4,547,913 A * | 10/1985 | Phillips ............... 623/27 |
| 4,619,661 A | 10/1986 | Axelsson |
| 4,636,220 A | 1/1987 | Ziegelmeyer |
| 4,645,509 A * | 2/1987 | Poggi et al. ............... 623/55 |
| 4,652,266 A | 3/1987 | Truesdell |
| 4,676,800 A | 6/1987 | Chen |
| 4,721,510 A | 1/1988 | Cooper et al. |
| 4,792,340 A | 12/1988 | Aulie et al. |
| 4,822,363 A | 4/1989 | Phillips |
| 4,865,612 A | 9/1989 | Arbogast et al. |
| 4,883,493 A | 11/1989 | Martel et al. |
| 4,892,553 A | 1/1990 | Prahl |
| 4,892,554 A | 1/1990 | Robinson |
| 4,911,724 A | 3/1990 | Fikes |
| 4,923,475 A | 5/1990 | Gosthnian et al. |
| 4,938,776 A | 7/1990 | Masinter |
| 4,938,777 A | 7/1990 | Mason et al. |
| 4,959,073 A | 9/1990 | Merlette |
| 4,994,086 A | 2/1991 | Edwards |
| 5,004,477 A | 4/1991 | Palfray |
| 5,007,938 A | 4/1991 | Prahl |
| 5,019,109 A | 5/1991 | Voisin |
| 5,037,444 A | 8/1991 | Phillips |
| 5,062,859 A | 11/1991 | Naeder |
| 5,066,305 A | 11/1991 | Firth |
| 5,071,435 A | 12/1991 | Fuchs et al. |
| 5,108,454 A | 4/1992 | Rotschild et al. |
| 5,112,356 A | 5/1992 | Harris et al. |
| 5,116,381 A | 5/1992 | Palfray |
| 5,116,384 A | 5/1992 | Wilson et al. |
| 5,116,385 A | 5/1992 | Allard et al. |
| 5,156,631 A | 10/1992 | Merlette |
| 5,156,632 A | 10/1992 | Wellershaus |
| 5,181,932 A | 1/1993 | Phillips |
| 5,219,365 A * | 6/1993 | Sabolich ............... 623/55 |
| 5,486,209 A | 1/1996 | Phillips |

FOREIGN PATENT DOCUMENTS

| | | |
|---|---|---|
| DE | 883321 | 7/1953 |
| DE | 179844 | 10/1954 |
| DE | 1179328 | 4/1957 |
| DE | 963849 | 5/1957 |
| DE | 1211354 | 2/1966 |
| DE | 2241971 | 3/1974 |
| DE | 2718395 | 9/1986 |
| EP | 331468 | 9/1989 |
| FR | 800547 | 7/1936 |
| FR | 2567395 | 1/1966 |
| FR | 25322 | 10/1972 |
| FR | 2501999 | 9/1982 |
| FR | 2506603 | 12/1982 |
| FR | 2626463 | 1/1988 |
| GB | 22172 | of 1898 |
| GB | 16750 | 12/1916 |
| GB | 120445 | 11/1917 |
| GB | 120462 | 11/1918 |
| GB | 275902 | 8/1927 |
| GB | 306313 | 4/1928 |
| GB | 621576 | 7/1946 |
| GB | 1371996 | 10/1974 |
| GB | 1432481 | 4/1976 |
| GB | 2092451 | 8/1982 |
| GB | 2124493 | 2/1984 |
| GB | 2 139 089 A * | 11/1984 ............... 602/23 |
| GB | 2202448 | 9/1988 |
| SE | 445515 | 6/1986 |
| SU | 397204 | 1/1974 |
| SU | 605613 | 4/1978 |
| SU | 778732 | 12/1980 |
| SU | 806023 | 2/1981 |
| SU | 1465045 | 3/1989 |
| SU | 1465046 | 3/1989 |
| SU | 1498490 | 8/1989 |
| SU | 1600759 | 10/1990 |
| WO | 8800815 | 7/1986 |
| WO | 8905617 | 12/1987 |
| WO | 8909036 | 10/1989 |
| WO | 89/09036 * | 10/1989 ............... 623/55 |

OTHER PUBLICATIONS

Copes/Bionic Ankle.

*L.A. Times* View Seection, "Seattle Foot," Jun. 12, 1984.

Campbell Childs, Jr. Product Catalog.

"The Flex–Shin: A composite material for Use in Flexible Shank Below–Knee Prosthesis," Thurston, et al., Prosthetics and Orthotics International.

Experimetnation Clinique D'Une Prothese De Membre Ingerieur En Materiaux Composites,: Andre Gueyraud, *University of Marseille,* 1987.

* cited by examiner

FOOT PROSTHESIS HAVING CURVED FOREFOOT

RELATED APPLICATIONS

This application is a continuation of U.S. application Ser. No. 08/727,772, filed Oct. 8, 1996, now U.S. Pat. No. 5,976,191, which is a continuation of U.S. application Ser. No. 08/532,530 filed Sep. 22, 1995, now U.S. Pat. No. 5,593,457, which is a continuation of U.S. application Ser. No. 08/270,231 filed Jul. 1, 1994, now U.S. Pat. No. 5,486,209, which is a continuation of U.S. application Ser. No. 07/977,654, filed Nov. 17, 1992, now abandoned, which is a continuation of U.S. application Ser. No. 07/337,374, filed Apr. 13, 1989, now U.S. Pat. No. 5,181,932.

BACKGROUND OF THE INVENTION

This invention relates to foot prostheses in general, and specifically to a prosthetic foot characterized by a unitary foot and heel construction, and/or an auxiliary ankle construction which permits the flexibility of the prosthesis to be selectively determined and easily changed. The invention also includes an improved coupling for attaching said foot prosthesis to an auxiliary pylon tube.

The prior art is replete with various types of mechanical devices purporting to solve the foot prosthesis problem. Typical of early devices if Lange U.S. Pat. No. 2,075,583, which incorporates a rubber form mounted in operative relationship with a rigid metallic core. Exemplary of the latest developments in the field is Poggi U.S. Pat. No. 4,645,509, which teaches a prosthetic foot incorporating a monolithic keel or beam of relatively massive proportions intended to react to the load of an amputee's body during walking, running, jumping, and the like and to release the resultant stored energy to create foot lift and thrust complementing the amputee's natural stride.

However, each of the prior art devices has significant deficiencies; specifically, the component parts of the prosthesis, as in Lange, are too heavy and too rigid or, as in Poggi, are too massive and monolithic to respond properly to the nuances of stress-response gradients characteristic of the human foot.

One of the primary factors which has inhibited the creation of a truly successful prosthetic foot has been the fixation of the prior art with the duplication of the structural aspects of the skeletal and muscular components of an actual human foot. In many instances, as exemplified by Poggi '509, mentioned hereinabove, even the toes of the foot are attempted to be duplicated by providing simulacra thereof. It is this fixation upon the mechanical elements of the human foot which has restricted the art to an attempt to duplicate the human foot components, a tendency which is particularly exemplified in Gajdos U.S. Pat. No. 3,335,428.

My copending application Ser. No. 07/293,824 discloses certain concepts relating to a prosthetic foot characterized by a forefoot portion and a heel portion which may be permanently or demountably associated with each other whereby both the forefoot portion and the heel portion can be readily exchanged with correspondingly constructed heel and forefoot portions. This exchangeability permits size adjustment or accommodation of different spring rates to suit the size of foot of the amputee or the stride and weight of the amputee, yielding an almost infinite range of combinations of spring rate and size to the amputee, and allowing a natural stride and resilience of gait which has not been obtainable by prior art prosthetic devices. Other than my present invention and my copending application, I am unaware of any prosthetic foot device incorporating such demountably attached forefoot and heel portions, and providing such ease and range of adjustability.

OBJECTS AND ADVANTAGES OF THE INVENTION

It is, therefore, an object of my invention to provide a foot prosthesis which is characterized by a foot portion and an ankle portion which may be permanently or demountably associated with each other, with the ankle portion having an upwardly extending attachment section providing ease of manufacture and resistance to rotation, whereby both the foot portion and the ankle portion can be readily exchanged with correspondingly constructed foot and ankle portions to provide size adjustment or accommodation of different spring rates to suit the size of foot of the amputee or the stride and weight of the amputee, and further adjustments can be made by the use of an auxiliary ankle spring member. Therefore, an almost infinite combination of spring rate and size can be provided to the amputee, achieving a natural stride and resilience of gait, which has not been obtainable by prior art prosthetic devices.

Another object of the invention is the provision in a prosthetic foot of the aforementioned character of an interchangeable or permanent foot portion which has a toe section, an arch section, and a heel section, all constructed without the necessity of tapering of the thickness thereof. Also incorporated in the aforementioned foot is an ankle portion which incorporates an upper attachment section, a curvilinear ankle section, and a lower attachment section secured to the intersection of the arch and toe sections of the foot portion. The previously mentioned heel section of the foot portion extends beyond the curvilinear ankle and attachment sections of the ankle portion.

As previously indicated, the ankle portion can be provided in different sizes and spring rates, and an auxiliary ankle member may be utilized, thus permitting the gait, weight, and activity level of the amputee to be readily accommodated. Correspondingly, the ankle portion can be demountably associated with the foot portion of the foot to permit different sizes of foot portion having different spring rates to be mounted in operative relationship with the ankle portion.

Another object of the invention is the provision of a prosthetic foot of the aforementioned character in which both the foot and ankle portions of the foot are fabricated, and the auxiliary ankle may be fabricated, from superimposed laminates maintained in operative relationship by an encapsulating polymer, and further in which said toe, arch and heel sections of said foot portion, said spring section of said ankle portion, and said auxiliary ankle attachment are susceptible to bending stress determined by the number of the laminates and polymers in the respective toe, arch and heel sections of said foot portion, in said spring section of said ankle portion, and in said auxiliary ankle attachment. Thus, the various portions and sections thereof are encapsulated in a polymer and capable of spring stress response as ankle loads are imposed thereupon during the utilization of said foot.

A further object of the invention is the provision, in a prosthetic foot of the aforementioned character, of a foot portion which consists of continuous, integrally and simultaneously formed toe, arch, and heel sections, said sections being fabricated as a unitary structure by polymer impregnation of superimposed reinforcing laminae maintained in the desired configuration of said foot portion and said toe, arch and heel sections being capable of spring stress generated energy storage whereby the subjection of the toe or heel sections to bending moments will cause uniform transmission of spring stress through said arch section and through said curvilinear ankle section of said ankle portion to said attachment section thereof.

Another object of the invention is the provision of the aforesaid prosthetic foot in which the ankle section of said ankle portion has its upper extremity constituted by said upper attachment section and its lower extremity extending into and constituting said lower attachment section, said lower extremity, said curvilinear ankle section and said upper attachment section maintaining an approximately uniform thickness transversely of the longitudinal axis of said sections. Similarly, said foot portion and its various sections are provided with an approximately uniform thickness transversely of the longitudinal axis of said sections.

A further object of the invention is the provision of the aforesaid auxiliary ankle attachment, which is associated with the ankle section of said ankle portion to increase the resistance of said ankle section to loads imposed upon the toe section of said foot portion. The concept of the auxiliary ankle involves the provision of ankle members characterized by different spring rates, which permits the resistance of the ankle section to deflection to be precisely adjusted to the weight, activity level and other characteristics of the individual for whom said foot is being adjusted.

The polymers utilized to encapsulate the fibrous laminae are characterized by elasticity and flexibility so that the foot and ankle portions deflect proportionally to the engagement of said foot portion with an adjacent surface, causing the resultant energy to be stored and subsequently released when the gait of the amputee incorporating thrust and lift components results in the utilization of the stored energy and a consequent reduction of the energy expended by the amputee. There is a gradual increase in stiffness as the lever arm of the toe section of the foot portion shortens due to gradual deflection thereof.

It is an additional object of my invention to provide an improved coupling mechanism for attaching a prosthetic foot of the abovementioned character to an auxiliary pylon tube which is in turn attached to the wearer's leg.

Another object of the invention is the provision in a prosthetic foot of the aforementioned character of a forefoot portion which incorporates an upwardly extending attachment section, a curvilinear ankle section, an arch section and a toe section. As previously mentioned, the forefoot portion can be provided in different sizes and spring rates, and an auxiliary ankle member may be utilized, thus permitting the gait, weight, and size of foot of the amputee to be readily accommodated. Also incorporated in the aforementioned foot is an interchangeable or permanent heel portion which has an attachment section secured to the intersection of the arch and toe sections of the forefoot portion and a heel section extending beyond the curvilinear ankle and attachment sections of the forefoot portion.

In order to impart a cosmetic aspect to the prosthetic foot, after proper fitting of the foot to insure that the foot and ankle portions and the auxiliary ankle are properly balanced and of appropriate size, the prosthesis may be encapsulated in a suitably shaped foot-like shroud to facilitate the utilization of the prosthetic foot with a conventional shoe. The enclosure must be sufficiently flexible so as not to inhibit the free movement and flexure of the foot and ankle portions and the auxiliary ankle of the prosthetic foot, but, because of the inherently resilient and stress-absorbing characteristics of said foot, little dependence is needed upon the ancillary cushioning action of the enclosure.

Consequently, the foot of my invention is characterized by extreme light weight, instantaneous response to imposed loads and correspondingly instantaneous delivery of stored energy when the gait of the wearer indicates that such stored energy is to be released. Moreover, the foot may be readily mounted in operative relationship with conventional ancillary pylons and couplings, and can be fine-tuned by the blending of the foot and ankle portions and auxiliary ankle characteristics to achieve the ultimate in operative response to the needs of the wearer.

Consequently, the wearer of the foot may engage in a wide variety of activities which were precluded in the past because of the structural limitations and corresponding performances of prior art prostheses. Running, jumping and other activities are sustained by the foot and it may be utilized in the same manner as the normal foot of the wearer.

Other objects and advantages of the invention will be apparent from the following specification and the accompanying drawings, which are for the purpose of illustration only.

DESCRIPTION OF PREFERRED EMBODIMENT OF THE INVENTION

Figure 1:
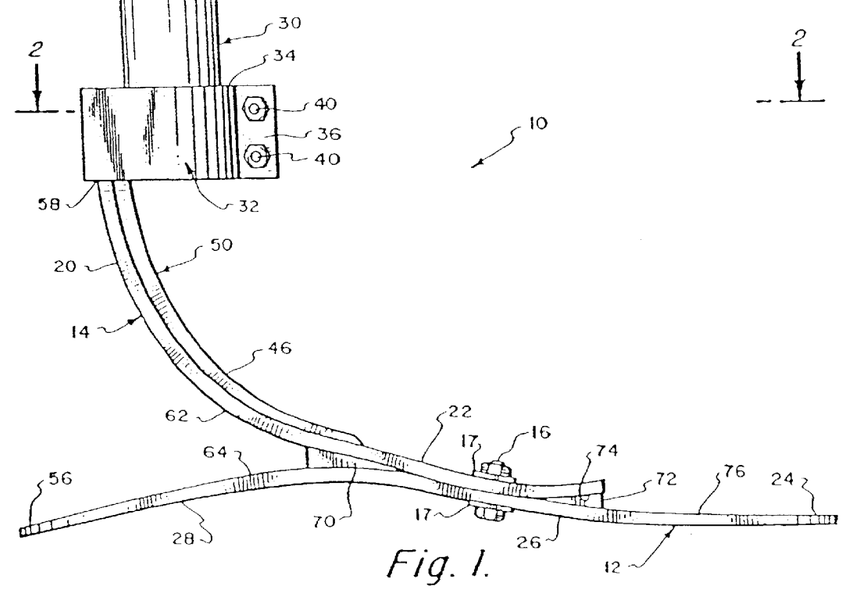
FIG. 1 is a side elevation view of portion of a prosthesis constructed in accordance with the teachings of the invention.
Figure 2:
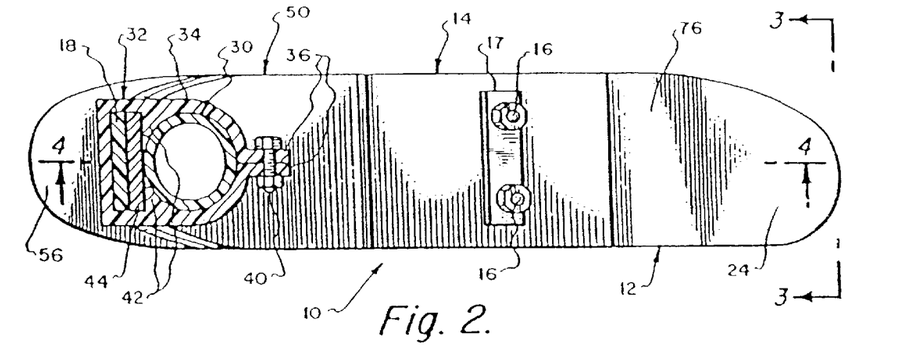
FIG. 2 is a partially sectional plan view, taken along line 2—2 of FIG. 1.

Referring to the drawings, and particularly to FIGS. 1 and 2 thereof, I show a foot prosthesis 10 constructed in accordance with the teachings of the invention and including a foot portion 12 and an ankle portion 14 operatively and demountably connected to each other by bolt and nut combinations 16 associated with load-transmitting metallic plates 17. If indicated, the foot and ankle portions can be permanently secured to each other, as by epoxy adhesive, an intermediate resilient member, or the like.

Figures 3, 4:
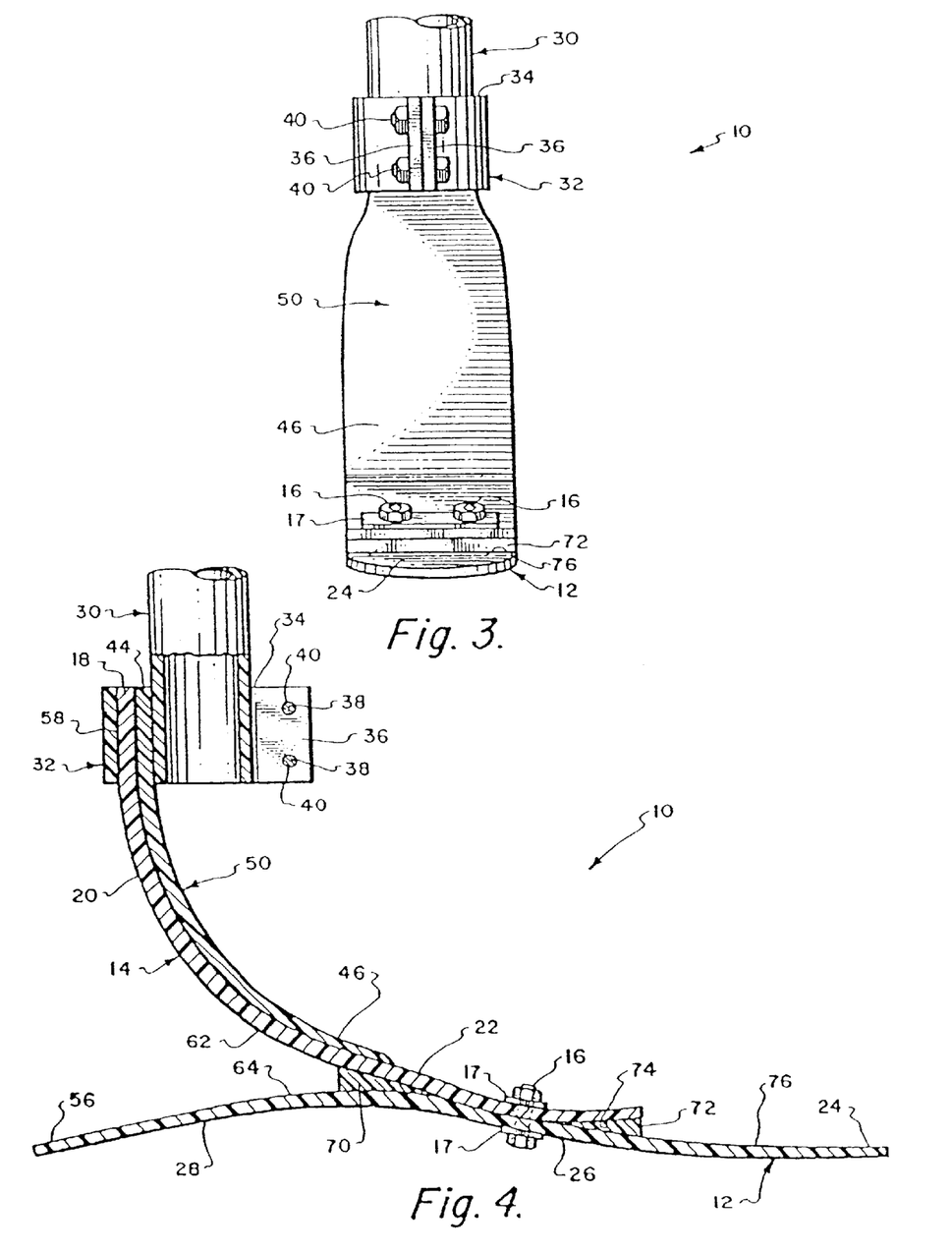
FIG. 3 is a front elevation view, taken along line 3—3 of FIG. 2.
FIG. 4 is a partially sectional side elevation view, taken along line 4—4 of FIG. 2.

The ankle portion 14 of the prosthesis 10 includes a substantially rigid upper attachment section 18, FIG. 4, a curvilinear ankle section 20, and a lower attachment section 22. The sections 18, 20, and 22 of the ankle portion 14 are formed integrally with one another and simultaneously by a plurality of juxtaposed, shaped laminae embedded in a hardened, flexible polymer.

The attachment section 18 has a rearward surface 58, as shown in FIG. 4, and a forward surface substantially parallel thereto. The attachment section 18 is substantially rigid and capable of sustaining torsional, impact and other loads impressed thereupon by the foot portion 12 and ankle portion 14 of the prosthesis 10. In addition, the inherent rigidity of the attachment section 18 prevents it from being distorted in any way and causes the effective transmission of the aforesaid loads imposed thereupon to a suitable ancillary prosthetic pylon 30, through a pylon coupling 32, constructed of graphite or some other appropriately strong material.

The pylon coupling 32 incorporates a split sleeve 34 which surrounds the attachment section 18, an auxiliary ankle member 50 (if any, as more thoroughly described below), and the prosthetic pylon 30. Tab members 36 are provided at the split in sleeve 34, and said tab members are provided with two centrally-located openings 38, FIG. 4, adapted to accommodate bolt and nut combinations 40. The bolt and nut combinations 40 can be tightened to cause the pylon coupling 32 to grip and cause a frictional engagement of the attachment section 18, the auxiliary ankle member 50, if any, and the prosthetic pylon 30.

The pylon coupling 32 further includes gripping means 42, shown in the preferred embodiment as angular projections located on the internal surface of the coupling 32 in the interstices between the ancillary prosthetic pylon 30 and the attachment section 18 or the auxiliary ankle member 50, if any. Gripping means 42 are so sized and shaped as to provide additional surface contact and improve the aforementioned frictional engagement between the coupling 32, the pylon 30, and the attachment section 18 or the auxiliary ankle member 50 if present.

As shown in the drawings of the preferred embodiment, the tab members 36 associated with the split in the coupling 32 are adjacent the front of the prosthetic pylon 30, but those skilled in the art will understand that the aforementioned split and the tab members 36 associated therewith may alternatively be oriented toward the side or rear of the prosthetic foot 10, and still be within the scope of the present invention.

As previously mentioned, an auxiliary ankle member 50 can be utilized to decrease the flexibility of the ankle portion 14. The auxiliary ankle 50 is formed from fibrous laminates of the same character as the various portions of the prosthesis 10. In the preferred embodiment, the auxiliary ankle 50 incorporates an attachment section 44 which is mounted inside the coupling 32, between the ancillary pylon 30 and the attachment section 18 of the ankle portion 14. The auxiliary ankle 50 is secured in operative relationship with the curvilinear ankle section 20 of ankle portion 14 through the aforementioned assembly of the coupling 32, which retains the various components in the aforesaid operative relationship. On its end opposite the attachment section 44, ankle member 50 has a tapered section 46 which provides a varying flexibility along the length of the ankle member 50 and also lessens the likelihood that the ankle member 50 will be undesirably snagged or restrained in its cooperative relationship with ankle portion 14 and the cosmetic cover of the prosthesis, more thoroughly discussed below. In alternative embodiments, as will be understood by those skilled in the art, such tapering is not required in order to practice the invention, and accordingly, the ankle member 50 can be provided with a relatively uniform thickness along the length thereof.

In the preferred embodiment, the auxiliary ankle member 50 is secured against the internal radius of the curvilinear ankle section 20, so that the anticipated upward deflection of a toe section 24 of the foot portion 12, as more thoroughly described below, will eventually cause deformation of the auxiliary ankle 50 as well as deformation of the ankle section 20, effectively combining the deformation resistance and energy storage characteristics of the auxiliary ankle member 50 with those of the ankle section 20. Alternative embodiments would include securing the auxiliary ankle 50 to the rearward surface 58 of the attachment section 18 and further securing the auxiliary ankle tapered section 46 to an under surface 62 of the ankle section 20 in order to achieve the aforedescribed desired combination of the deformation resistance and energy storage characteristics of the auxiliary ankle member 50 with those of the ankle section 20.

The auxiliary ankle member 50 can be provided with different numbers of laminates to make it more or less compliant to loads transmitted through the ankle section 20. Consequently, when confronted with various anomalies in an amputee, such as overweight or excess activity levels, the basic structure of the ankle portion 14, and more particularly the ankle section 20, can be materially modified to provide ankle portion action which is precisely adjusted to the needs of the amputee. Moreover, a variety of auxiliary ankle members 50 can be made available to an amputee, allowing the flexibility of the prosthesis to be adjusted on the basis of the particular activity which the amputee is undertaking.

As previously mentioned, a cosmetic cover, not shown, can be provided to shroud the prosthesis 10 after the optimum assemblage of the foot and ankle portions 12 and 14 and any auxiliary ankle member 50 has been accomplished. Unlike prior art constructions, however, the cosmetic cover, which may be formed of low-density formed polymer, is not required to serve any ancillary shock-absorbing or other stress-isolating function since all of the loads imposed upon the prosthesis can be absorbed, transmitted and reasserted in a manner to be described in greater detail below.

The bolt and nut combinations 16, in conjunction with the load-distributing metallic plates 17, serve to secure the ankle portion 14 in operative relationship with the foot portion 12 of the prosthesis 10, as best shown in FIGS. 1–2 of the drawings. The aforesaid mode of affixation facilitates the assembly or dismounting of selected ankle portions 14 in operative relationship with selected foot portions 12 of the prosthesis 10, thus permitting a wide range of different sizes and stress load response characteristics to be related to each other to accomplish the optimum functional correspondence between the foot and ankle portions 12 and 14 to accommodate to the maximum extent the needs of the wearer of the prosthesis, and, also, to provide for a proper mating of the prosthesis 10 with a selected, ancillary pylon 30 or the like.

The foot portion 12, as best shown in FIG. 1 of the drawings, includes a toe section 24, an arch section 26, and a heel section 28 which has its rearward extremity 56 extending beyond the extreme rearward surface 58 of the ankle portion attachment section 18 of the prosthesis 10. Mating bores, not shown, in the arch section 26 of the foot portion 12 and the ankle portion 14 receive the respective bolt and nut combinations 16 to provide for the aforesaid facility in assembling and disassembling of the foot and ankle portions 12 and 14. In the preferred embodiment, the various sections of the foot portion 12 are all constructed without the necessity of tapering of the thickness thereof, although those skilled in the art will understand that the invention is not limited to such non-tapering construction.

Interposed between the under surface 62 of the ankle section 20 of the ankle portion 14 and an upper surface 64 of the heel section 28 is a resilient, spring action function block 70 of wedge-shaped configuration to determine the lever arm of the heel section 28 and isolate the under surface 62 of the ankle section 20 and the upper surface 64 of the heel section 28 from each other. The function block 70 may be fabricated from a wide variety of resilient materials, including natural and synthetic rubbers, or the like.

Similarly, a second spring action function block 72 of like shape and construction can be interposed between an under surface 74 of the lower attachment section 22 of the ankle portion 14 and an upper surface 76 of the toe section 24 to determine the lever arm of the toe section 24 and isolate the under surface 74 of the lower attachment section 22 and the upper surface 76 of the toe section 24 from each other.

The materials from which the foot portion 12 and ankle portion 14 and the auxiliary ankle 50 are fabricated must be such as to provide an energy-storing, resilient, spring-like effect. This is necessary because each engagement of the prosthesis 10 with an adjacent surface impresses compression, torsional and other loads upon the prosthesis 10 which must be stored within the prosthesis and then, dependent upon the stride of the wearer, be reimpressed upon said surface to achieve a natural stride conforming, ideally, in all respects to the stride of the unimpaired limb of the wearer of the prosthesis 10.

The foot and ankle portions 12 and 14 and the auxiliary ankle 50 of the prosthesis are preferably molded as unitary components and are carefully formed to provide for uniform absorption of stress imposed thereupon. The configuration of both portions 12 and 14 is of utmost importance and the laminates and the polymer or polymers from which the portions 12 and 14 are fabricated must be resilient and capable of absorbing the compressive, torsional and other stresses referred to hereinabove and of restoring the stored energy created by such stresses, in a natural manner, to the impacted surface which originally imposed such stresses upon the prosthesis 10.

It has been found that there is a limited number of polymers capable of sustaining the significant stresses and repetitive loads imposed upon the prosthesis 10, particularly in the light of the countless numbers of cycles to which the prosthesis 10 is subjected during normal, everyday use.

At present, the best materials for the prosthesis are a composite of high-strength graphite fiber in a high-toughness epoxy thermosetting resin system. There are several reasons for this: (1) high strength; (2) stiffness to weight ratio of graphite as compared to other materials; (3) the almost complete return of input or stored energy; (4) light weight; (5) high fatigue strength; and (6) minimal creep. As an alternative material, fiberglass/epoxy is a fair choice, but it is not as good as graphite because of lower fatigue strength and higher density. Kevlar is even less acceptable due to poor compression and shear strength, although it is the lowest density of those mentioned.

An important aspect of the polymers and laminates referred to hereinabove is that they are characterized by needed, but not excessive, flexural deflection under load, which characteristic permits the shock-absorption stress loading of the prosthesis 10 while maintaining sufficient stability to prevent the collapse of the foot and ankle portions 12 and 14 and the ankle member 50 of the prosthesis 10 while loads are imposed thereupon.

To achieve the relatively thin construction of the foot and ankle portions 12 and 14 and the auxiliary ankle member 50 of the prosthesis 10, the aforesaid polymers are utilized in conjunction with various laminating materials. Various types of fibrous laminae can be utilized to achieve the continuum required by the design of the foot and ankle portions 12 and 14 and the ankle member 50 to complement the stress-absorbing and storing characteristics of the polymers in which said fibrous laminae are embedded.

Of course, there is a wide variety of fibrous reinforcements in the form of laminae available at the present time, including such inorganic fibers as glass or carbon fibers. These inorganic fibers are customarily provided in tape or sheet form and can be readily superimposed in the mold to permit them to be encapsulated in the selected polymer.

Obviously, the number of superimposed laminae and the lengths thereof, together with the thickness of the encapsulating polymer, determine the stress characteristics of the resultant foot and ankle portions 12 and 14 and the ankle member 50 and, correspondingly, determine the total weight of the prosthesis 10. As will be apparent from the discussion hereinbelow, the individual foot and ankle portions 12 and 14 and ankle member 50 are designed to specifically accommodate individuals having different foot sizes, different weights and different strides and the individual design of the foot and ankle portions 12 and 14 and the ankle member 50 provides for matching, to an extent previously unknown in the art, the natural characteristics of the wearer's uninjured limb.

Furthermore, the function blocks 70 and 72 can be provided in different sizes and in materials having different compression characteristics so that the respective lever arms and the corresponding deflections of the heel section 28 and the toe section 24 may be increased or decreased.

As previously mentioned, the ankle section 20 is formed integrally with the upper attachment section 18 and said attachment section constitutes the upper extremity of the ankle section 20, while the initiation of the lower attachment section 22 of the ankle portion 14 constitutes the lower extremity of the ankle section 20. The configuration of the ankle section 20, in conjunction with the auxiliary ankle member 50, is the means whereby compressive loads imposed during impingement of the foot and ankle portions 12 and 14 upon an adjacent surface are absorbed and subsequently reimposed upon said surface. The ankle portion 20 and the auxiliary ankle member 50 are so designed that they function, substantially, as an ankle joint to permit pivoting of the foot portion 12 thereabout in a manner analogous to the manner in which the normal foot pivots about the normal ankle joint on an axis transversely of said ankle joint.

The radii of curvature of the ankle section 20 and any auxiliary ankle member 50 correspond to provide for the inherent resilience and deflection of the foot portion 12 while inhibiting undesired, excessive collapse of the ankle section 20.

It will be noted that the arch section 26 of the foot portion 12 is substantially rigid and that the initial deflection of the heel section 28 occurs immediately adjacent the rearward extremity 56 of said heel section, terminating immediately adjacent the function block 70. Obviously, a greater length or less resilient function block 70 reduces the lever arm of the heel section 28 of the foot portion 12 and correspondingly reduces the modulus of deflection of said ankle section, while a smaller length or more resilient function block 70 increases the lever arm and correspondingly increases the deflection of the heel section 28 under load. The length of the second function block 72 likewise affects the lever arm and deflection of the toe section 24 of the foot portion 12.

The toe section 24 and heel section 28 can be provided in different lengths to correspond to the size of the foot of the wearer of the prosthesis 10. When such different lengths are provided, corresponding reduction or increase in the number of laminae and thickness of taper of the respective toe section 24 and heel section 28 can be made to provide for the proper flexure of said toe and ankle sections. It should also be noted that, even with the shortest heel section 28, the rearward extremity 56 thereof projects beyond the rearward surface 58 of the ankle portion 14. Consequently, the stabilizing and stress-absorption characteristics of the heel section 28 of the prosthesis 10 are always maintained.

In an alternative embodiment, shown in FIGS. 5–8, a toe section 82 can be incorporated into an ankle portion 80, and a heel portion 84 can be permanently or detachably associated therewith to practice certain aspects of the invention. Except for the toe section 82 being attached to the ankle portion 80 rather than the heel portion 84, the alternative embodiment of FIGS. 5–8 is constructed and functions similarly to the preferred embodiment described above. An auxiliary ankle member 86, similar to configuration and function to ankle member 50 in the preferred embodiment, may be utilized to achieve the benefits associated with ankle member 50 in the preferred embodiment. FIGS. 5–8 further now an alternative embodiment of a coupling 90 suitable for joining the ankle portion 80, the auxiliary ankle member 86, and the pylon 30 in operative engagement. Those skilled in the art will understand that many alternative embodiments of the coupling can be constructed and practiced interchangeably in connection with the many alternative embodiments of the rest of the invention.

The ankle portion 80 of the alternative embodiment of the prosthesis includes a substantially rigid attachment section 92, a curvilinear ankle section 94, an arch section 96 and a toe section 82. The sections 92, 94, 96 and 82 of the ankle portion 80 are formed integrally with one another and simultaneously by the incorporation of a plurality of laminae embedded in a hardened, flexible polymer.

Figures 7, 8:
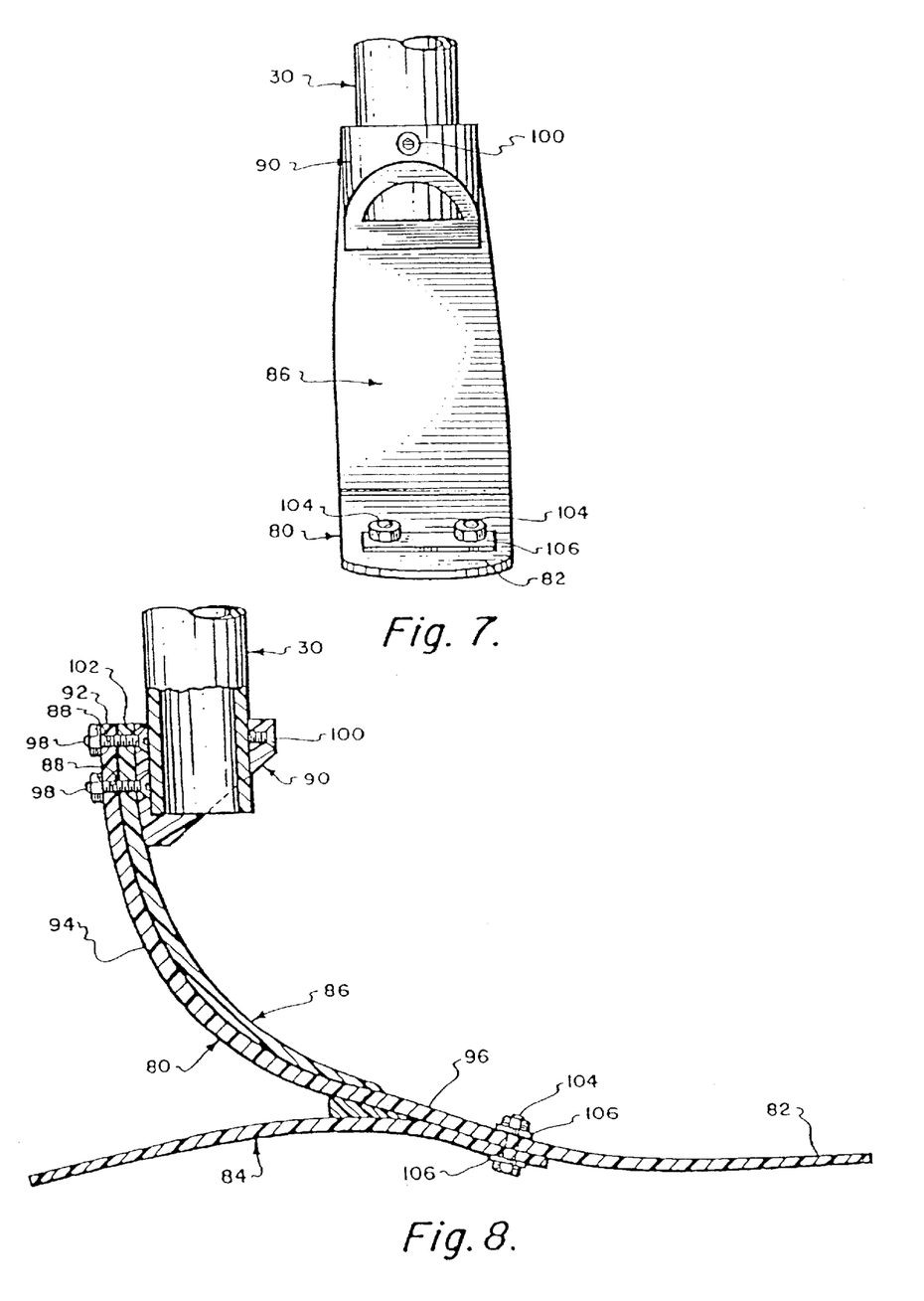
FIG. 7 is a front elevation view, taken along line 7—7 of FIG. 6.
FIG. 8 is a partially sectional side elevation view, taken along line 8—8 of FIG. 6.

The attachment section 92 incorporates two centrally-located openings 88, FIG. 8. The attachment section 92 is substantially rigid and capable of sustaining torsional, impact and other loads impressed thereupon by the ankle portion 80 and heel portion 84 of the prosthesis. In addition, the inherent rigidity of the attachment section 92 causes the effective transmission of the aforesaid loads imposed thereupon to a suitable ancillary prosthetic pylon 30, by bolt and nut combinations 98 assembled through openings 88 to a pylon coupling 90. A screw 100 or other suitable attachment means secures the ancillary pylon 30 in the coupling 90.

In the particular alternative embodiment of FIGS. 5–8, the auxiliary ankle 86 is mounted between coupling 90 and ankle portion 80, and is secured in operative relationship with the ankle section 94 of ankle portion 80 through the use of centrally-located openings in an attachment section 102 of the auxiliary ankle member 86, which openings are substantially aligned with openings 88 of the ankle portion attachment section 92. Bolt and nut combinations 98 retain the various components in the aforesaid operative relationship. Alternative embodiments would include securing the auxiliary ankle 86 to the rearward surface of the attachment section 92 as described above for the preferred embodiment.

Figure 5:
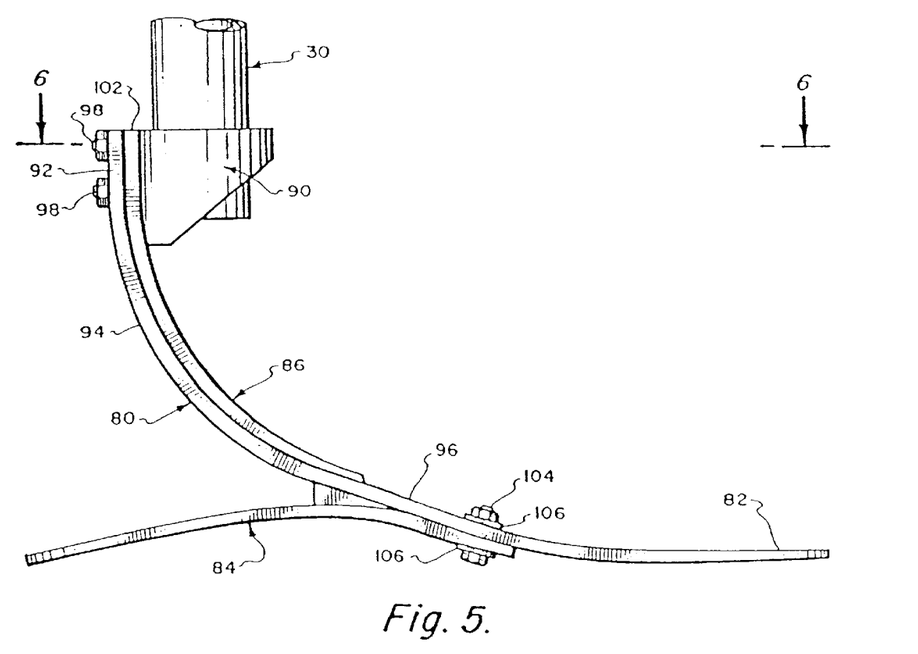
FIG. 5 is a side elevation view of portion of an alternative embodiment of a prosthesis constructed in accordance with the teachings of the invention.
Figure 6:
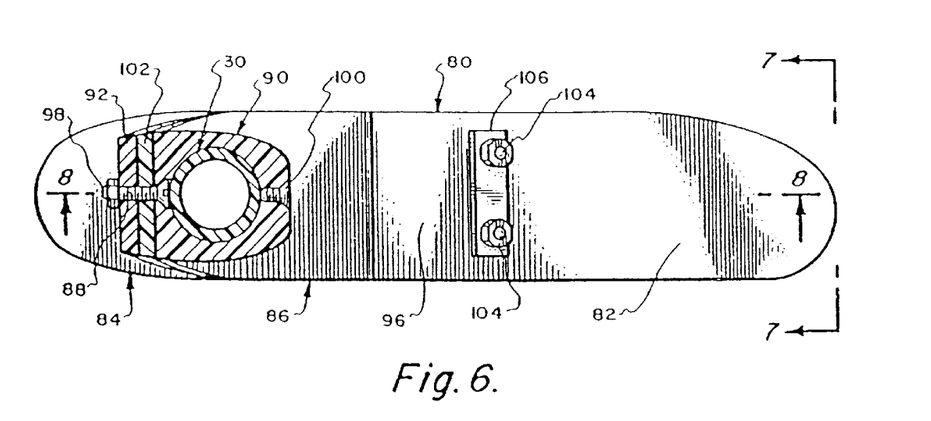
FIG. 6 is a partially sectional plan view, taken along line 6—6 of FIG. 5.

In this alternative embodiment, bolt and nut combinations 104 similar to the combinations 16 in the preferred embodiment, in conjunction with the load-distributing metallic plates 106 similar to the plates 17 in the preferred embodiment, serve to secure the heel portion 84 in operative relationship with the ankle portion 80 of the prosthesis, as best shown in FIGS. 5–6 of the drawings. The aforesaid mode of affixation facilitates the assembly or dismounting of selected heel portions 84 in operative relationship with selected ankle portions 80, thus permitting a wide range of different sizes and stress load response characteristics to be related to each other to accomplish the optimum functional correspondence between the ankle and heel portions 80 and 84.

It will, of course, be obvious to those skilled in the art that, with respect to any embodiment of the invention, the fibrous reinforcements in the form of laminae plies encapsulated in the prosthesis may be fayed or tapered to accomplish a gradual transition as the number of plies is reduced in any area of the foot or ankle portions.

Moreover, if a relatively lightweight individual partakes in sports or other activities which subject the prosthesis 10 to greater loads, an ankle or foot portion 14 or 12 will be fitted which will accommodate for those greater loads.

The ankle section 20 of the ankle portion 14 deflects under load and the auxiliary ankle member 50 similarly deflects. Additionally, the toe and heel sections 24 and 28 of the foot portion 12 deflect under such load. Therefore, when subjected to vertical compression loads, the ankle section 20, the auxiliary ankle member 50, and the toe and heel sections 24 and 28 absorb such loads.

Consequently, there is no stress concentration, either in the impact phase when the adjacent surface is initially contacted by the wearer of the prosthesis 10, or when return of the accumulated forces stored in the prosthesis 10 is accomplished.

The curvature of the toe section 24 provides for maximum accommodation of said section during surface contact in both the impact and delivery phases of the prosthesis 10. Similar considerations apply to the curvature of the heel section 28 of the foot portion 12 of the prosthesis 10. It will be noted that the arcuate, parabolic curvatures of the toe and heel sections 24 and 28 of the foot portion 12 provide for relatively extended lever arms which achieve stability and, also, stress storage and stress reaction.

The preferred method of manufacturing the foot and ankle portions 12 and 14 and the auxiliary ankle member 50 of the prosthesis 10 is by a thermosetting molding process including the utilization of molds having properly shaped and sized cavities. The cavities are designed to receive the requisite number of laminates and the proper volume of polymer.

Unlike prior art unitary devices, the fitting of the prosthesis 10 involves the judicious adjustment of the prosthesis by the proper combination of foot and ankle portions 12 and 14 and auxiliary ankle member 50, respectively. It also involves the selection of the properly designed ancillary pylon 30 which can be secured by means of the coupling 32 to the attachment section 18 of the ankle portion 14. Only when the proper correlation between the foot portion 12, ankle portion 14, auxiliary ankle member 50, and ancillary pylon 30 has been accomplished, can the cosmetic shroud, not shown, be installed upon the assembled, respective portions of the prosthesis 10.

By the prosthesis of my invention I provide a foot which can be carefully matched to the weight, stride and physical characteristics of the wearer. This is accomplished by carefully balancing the respective physical characteristics of the foot portion 12, the ankle portion 14, the auxiliary ankle member 50, and the various sections thereof.

Moreover, the assembled prosthesis is far lighter in weight than prior art prostheses since the inherent design and structure of the prosthesis, the materials used and the careful calculation of stress factors of the components of the prosthesis permit fine-tuning of the prosthesis of the needs of the wearer thereof.

I claim:

1. A lower limb prosthesis for providing resilient kinematic support to an amputee during normal walking, running and jumping activities, comprising:

a substantially rigid pylon member having a proximal end and a distal end extending substantially vertically downward and terminating at about the location of a natural human ankle joint, said pylon member configured to support the amputee's weight under longitudinal compression; and a flexible forefoot member configured to be selectively attached and detached to said distal end of said pylon member for providing substantially the sole support for all vertical, transverse and torsional loads transmitted by said pylon member, said forefoot member comprising:

an upper attachment section having a substantially flat vertically oriented attachment surface adapted to attach said forefoot member to said pylon member, said attachment surface comprising substantially the sole attachment surface of said forefoot member attaching said forefoot member to said pylon;

an intermediate section formed integrally with and curving substantially continuously downward and forward from said upper attachment section; and a lower section formed integrally with said intermediate section and curving substantially continuously forward therefrom defining a forward lever arm;

whereby said forefoot member can be selected to have desired kinematic resiliency characteristics so as to sustain a wide range of varying activities.

2. The lower limb prosthesis of claim 1, wherein said prosthesis is constructed of high-strength graphite fiber disposed in a high-toughness epoxy thermosetting resin.

3. The lower limb prosthesis of claim 1 further comprising a coupling member adapted to secure said forefoot member to said distal end of said pylon member.

4. The lower limb prosthesis of claim 1 further comprising an auxiliary support member attached at one end between said upper attachment section of said forefoot member and said distal end of said pylon member and extending downward and forward therefrom to reinforce said intermediate section, said auxiliary support member and said intermediate section cooperating to determine the bending characteristics of said forefoot member.

5. The lower limb prosthesis of claim 4 wherein said auxiliary support member is tapered to provide varied resistance to bending of said intermediate section of said forefoot member.

6. The lower limb prosthesis of claim 1 wherein said upper attachment section, said intermediate section and said lower section of said forefoot member are monolithically formed from superimposed laminates maintained in operative relationship by an encapsulating polymer.

7. The lower limb prosthesis of claim 1 wherein said upper attachment section is adapted to attach said forefoot member to a back surface of said pylon member.

8. The lower limb prosthesis of claim 1 further comprising a heel member attached to said flexible forefoot member and extending rearward therefrom defining a rearward lever arm.

* * * * *